United States Patent [19]

Woodruff et al.

[11] Patent Number: 4,975,111

[45] Date of Patent: Dec. 4, 1990

[54] ANTIALGAL COMPOSITIONS COMPRISING DIPHENYLETHERS AND ISOTHIAZOLONES, METHODS OF CONTROLLING ALGAE, AND COATING COMPOSITIONS COMPRISING THE ANTIALGAL COMPOSITIONS

[75] Inventors: Robert A. Woodruff, Buckingham, Pa.; Samuel E. Sherba, Willingboro, N.J.

[73] Assignee: Rohm and Haas Company, Philadelphia, Pa.

[21] Appl. No.: 315,628

[22] Filed: Feb. 24, 1989

[51] Int. Cl.$^5$ ............................... A01N 9/24
[52] U.S. Cl. ..................... 71/67; 71/DIG. 1
[58] Field of Search .................... 71/67, DIG. 1

[56] References Cited

U.S. PATENT DOCUMENTS

| | | | |
|---|---|---|---|
| 3,506,720 | 4/1970 | Model et al. | 568/637 |
| 3,629,477 | 12/1971 | Model et al. | 424/340 |
| 3,772,445 | 11/1973 | Noguchi et al. | 424/340 |
| 3,787,217 | 1/1974 | Nitta et al. | 71/67 |
| 3,798,276 | 3/1974 | Bayer et al. | 260/612 R |
| 3,908,019 | 9/1975 | Noguchi et al. | 424/340 |
| 4,112,002 | 9/1978 | Schneider et al. | 260/612 R |
| 4,243,403 | 1/1981 | Lewis et al. | 71/67 |
| 4,268,693 | 5/1981 | Muntwyler et al. | 568/637 |
| 4,339,462 | 7/1982 | Muntwyler et al. | 424/340 |
| 4,772,744 | 9/1988 | Bayer et al. | 560/133 |

FOREIGN PATENT DOCUMENTS

| | | | |
|---|---|---|---|
| 48-48624 | 7/1973 | Japan. | |
| 1592011 | 7/1981 | United Kingdom | 71/67 |

OTHER PUBLICATIONS

S. D. Strauss & P. R. Puckorius, Power, S1, "Cooling-water Treatment for Control of Scaling, Fouling, Corrosion", Jun. 1984.
Seventh Annual Congress on Marine Corrosion & Fouling, "Selecting Acting Antifouling Agents", Valencia, Spain, 11/10/88.
Boger et al., "Binder and Peroxidative Action of Oxyfluorfin in Sensitive and Tolerant Agent Species", Z. Naturforsch, 42c, 819 (1987).
Boger et al., "Multifunctional Mode of Action of Substituted Nitrodiphenylethers in Scenedesmus Cells", Z. Naturforsch, 36c, 633 (1981).
Boger et al., "Radical Formation and Peroxidative Activity of Phytotoxic Diphenyl Ethers", Z. Naturforsch, 39c, 486 (1984).
Boger et al., "Variable Fluorescence and Fluorescence Spectra of Algae after Herbicide-Induced Pigment Bleaching", Z. Naturforsch, 38c, 556 (1983).
Boger et al., "Oxyfluorfen and Lipid Peroxidation: Protein Damage as a Phytotoxic Consequences", Weed Science, 33, 766 (1985).
Boger et al., "Comparison of the Bleaching Activity of Norflurozon and Oxyfluorfen", Weed Science, 31, 338 (1983).
Boger et al., "Sites of Herbicidal Action on Photosynthesis: A Fluorescence Assay Study", Weed Science, 29, 371 (1981).
Boger et al., "The Bleaching Effect of the Diphenyl Ether Oxyfluorfen", Weed Science, 29, 169 (1981).
Boger et al., "Herbicidal Mode of Action of Chlorophyll Formation", J Agric Food Chem, 32, 868 (1984).
Boger et al., "The Diphenyl Ether Herbicide Oxyfluorfen: Action of Antioxidants", J Agric Food Chem, 32, 725 (1984).
Boger et al., "Peroxidative Activity of Oxyfluorfen with Regard to Carotenoids in Scenedesmus", J Agric Food Chem, 32, 523 (1984).
Boger et al., "Inhibition of Carotenogenesis by Substituted Diphenyl Ethers of the m-Phenoxybenzamide Type", Pesticide Biochemistry and Physiology, 20, 183 (1983).
Boger et al., "Correlation between Structure and Phytotoxic Activities of Nitrodiphenyl Ethers", Pesticide Biochemistry and Physiology, 19, 309 (1983).
Boger et al., "Mode of Action of Nitrodiphenylethers Affecting Pigments and Membrane Integrity", IUPAC Pesticide Chemistry, vol. 3, 97–102 (1983).
Boger et al., "Structure and Activity in Herbicidal Bleaching", IUPAC Pesticide Chemistry, vol. 1, 321–326 (1983).
Boger et al., "Formation and Degradation of Photosynthesis Membranes Determined by S-Labeled Sulfotyped", Plant Science Letters, 24, 347 (1982).

Primary Examiner—Richard L. Raymond
Assistant Examiner—Raymond Covington
Attorney, Agent, or Firm—Michael B. Fein

[57] ABSTRACT

Disclosed herein is a composition useful for controlling algae comprising (A) a compound of the formula

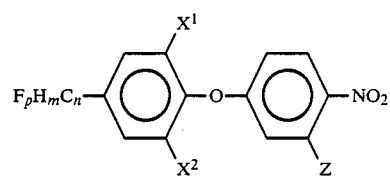

wherein
$X^1$, $X^2$ are independently selected from hydrogen, halogen, trihalomethyl, cyano, and ($C_1$ to $C_4$) alkyl;
Z is selected from the group consisting of hydrogen, halogen, cyano, carboxy or salt thereof, alkylthio, carbalkoxy, carboxyalkyl, carbalkoxyalkyl, carbalkoxyalkoxycarbonyl, carbalkoxyalkoxy, alkoxy, cycloalkoxy, alkenyl, alkyl, cycloalkyl, unsubstituted or substituted amino, $R^2O$ in which $R^2$ represents a hydrogen atom or the esterbonded acid radical of an inorganic or organic oxyacid and acyloxy;
p is an integer from 1 to $2n+1$;
m is an integer of 0 to $2n$;
n is an integer of 1 to 5;
$m+p=2n+1$
and (B) a 3-isothiazolone.

24 Claims, No Drawings

ANTIALGAL COMPOSITIONS COMPRISING DIPHENYLETHERS AND ISOTHIAZOLONES, METHODS OF CONTROLLING ALGAE, AND COATING COMPOSITIONS COMPRISING THE ANTIALGAL COMPOSITIONS

BACKGROUND OF THE INVENTION

1. Field of the Invention

The present invention relates to antialgal compositions, methods of controlling algae, and coating compositions comprising the antialgal compositions.

2. Description of the Prior Art

The presence of algae in various aqueous systems such as latices, paints, coatings, cooling water systems, decorative ponds and the like, can cause deterioration or disfigurement of these systems. For example, painted surfaces may be disfigured by the unsightly buildup of algae, thus detracting from the overall aesthetics of the painted article; cooling towers may lose efficiency due to the buildup of algae on surfaces, thus reducing the heat transfer capabilities of the tower. It is conventional to practice methods which inhibit the algal deterioration of such systems by incorporating a variety of additives or combination of additives that are characterized by having antialgal activity.

A wide variety of materials have been used to control algae in different environments, some of which are: chlorine/bromine compounds, glutaraldehyde, isothiazolones, organotin formulations, copper salts, quaternary ammonium compounds (SD Strauss and PR Puckorius in J. Power, S1, June 1984), and triazines. Each has deficiencies related to toxicity, pH and temperature sensitivity, limited effectiveness, chemical stability, and/or compatibility.

Different diphenylethers ("DPEs") have been found to have widely different antimicrobial properties. See, for example, halogenated hydroxy (acyloxy) DPEs (U.S. Pat. Nos. 3,506,720, 3,629,477, 4,268,693, 4,339,462), substituted nitro/halo DPEs (U.S. Pat. Nos. 3,772,445, 3,908,019), and nitro/trifluoromethyl DPEs (U.S. Pat. No. 4,112,002).

U.S. Pat. No. 3,787,217 and Japanese Kokai Patent Application No. 48-48624 to Nitta et al are directed towards the use of halogenated and alkyl substituted DPEs as paint antifouling agents and disclose the use of these materials to control growth of clams, barnacles, and shellfish larvae at 0.5–1.0 ppm dosage levels. These patents do not, however, teach or suggest the use or efficacy of substituted fluoroalkyl DPEs.

Great Britain Patent No. 1592011 to Ciba-Geigy discloses the use of DPEs containing amino (or substituted amino) or hydroxy (or ester derivatives of organic/inorganic acids) substituents as algicides, particularly dichloro- and trichloro-substituted DPEs. This patent does not, however, teach or suggest the use of fluoroalkyl DPEs without hydroxy or amino substituents.

On the other hand, J. Lorenz discloses that acifluorfen (2-chloro-4-trifluoromethylphenyl-3′-carboxy-4′-nitrophenylether, sodium salt) is ineffective at all levels tested on 10 different types of algae in a screening study of commercial herbicides for use as additives in antifouling paints ("Selective Acting Antifouling Additives," Seventh Annual Congress on Marine Corrosion and Fouling, Valencia, Spain, Nov. 10, 1988).

Numerous agricultural herbicides are known to be effective in controlling specific nuisance plants (weeds), crops, etc. The modes of action of such agricultural herbicides have been extensively studied and reported in the following references: Boger et al (Z. Naturforsch, 42c, 819 (1987), 36c, 633 (1981), 39c, 486 (1984), 38c, 556 (1983); Weed Science, 33, 766 (1985), 31, 338 (1983), 29, 371 (1981), 29, 169 (1981); J Agric Food Chem, 32, 868 (1984), 32, 725 (1984), 32, 523 (1984); Pesticide Biochemistry and Physiology, 20, 183 (1983), 19, 309 (1983); IUPAC Pesticide Chemistry, Vol 3, 97–102 (1983), Vol 1, 321–326 (1983); Plant Science Letters, 24, 347 (1982). These articles report studies on the primary modes of action using a model alga, Scenedesmus acutus, to provide quick and reliable measures for understanding structure-reactivity relationships among major known herbicides, including a variety of DPEs. Boger et al observed the effect of many DPEs against various physiological and biochemical processes, concluding that it was not clear which structures are necessary to affect various modes of herbicidal action: inhibition of photosynthetic electron transport, energy transfer inhibition, and peroxidative destruction of photosynthetic membranes. The parameters measured in the mode of action studies were pigment loss (bleaching effects), short-chain hydrocarbon production due to fatty acid oxidation, reduction of photosynthetic oxygen evolution, etc. Thus, Boger et al taught that phytotoxic effects are due to the influence of more than a single biochemical mode of action. Structurally different DPEs brough about similar responses among the parameters studied by Boger et al. The relative potential of given DPEs or other herbicides to alter electron transport, peroxidation, or energy transfer modes of action is not necessarily indicative of herbicidal effectiveness. In summary, although Boger et al disclose possible pathways for herbicidal modes of action, they do not teach or suggest the use of any of these DPEs to control algae in their natural environment where water solubility, alkaline pH stability characteristics, etc., are important variables. The algae used in the Boger et al studies served only as a model to illustrate different biochemical modes of action operable with a variety of known herbicides.

Based on the aforementioned performance deficiencies of conventional antialgal compounds there is a need for more effective antialgal agents that can be used at lower dosage rates, thus being more cost effective for the end user, reducing the pollution load on the affected environmental systems, and reducing the side effects to nearby non-target organisms, such as fish, useful crops, etc.

SUMMARY OF THE INVENTION

It is an object of this invention to provide a method of controlling algae at very low levels of active ingredient. It is a further object to use compositions which are compatible with a variety of systems susceptible to deterioration by algae. Another object is to provide a method of controlling algae in cooling towers, paints, marine antifoulant coatings, spray washes, swimming pools, coatings, decorative ponds and the like, without objectionable by-product odors, discoloration, or otherwise detrimental effects on the treated (and controlled) systems. These objects, and others which will become apparent from the following disclosure, are achieved by the present invention which is, in one aspect a composition useful for controlling algae comprising (A) a compound of the formula

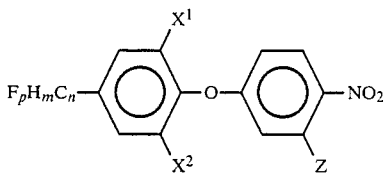

wherein
$X^1$, $X^2$ are independently selected hydrogen, halogen, trihalomethyl, cyano, or ($C_1$–$C_4$) alkyl, and
Z is selected from the group consisting of hydrogen, halogen, cyano, carboxy or salt thereof, alkylthio, carbalkoxy, carboxyalkyl, carbalkoxyalkyl, carbalkoxyalkoxycarbonyl, carbalkoxyalkoxy, alkoxy, cycloalkoxy, alkenyl, alkyl, cycloalkyl, unsubstituted or substituted amino, $R^2O$ in which $R^2$ represents a hydrogen atom or the ester bonded acid radical of an inorganic or organic oxyacid;
p is an integer from 1 to $2n+1$;
m is an integer of 0 to $2n$;
n is an integer of 1 to 5;
$m+p=2n+1$
and (B) a 3-isothiazolone.

In another aspect, the invention comprises a method of controlling algae comprising using an effective amount of the aforementioned composition.

Another aspect of the invention is a method of controlling algae in cooling tower water comprising maintaining a concentration of the aforementioned composition in the water.

In another aspect, the invention comprises a method of imparting algal resistance to a coating or impregnant composition comprising incorporation of the antialgal composition in the coating or impregnant.

The invention also comprises algae-resistant coating or impregnant compositions and marine antifoulant compositions comprising the antialgal composition.

DETAILED DESCRIPTION OF THE INVENTION AND THE PREFERRED EMBODIMENTS

We have discovered an especially effective composition useful for controlling algae comprising (A) a compound of the formula

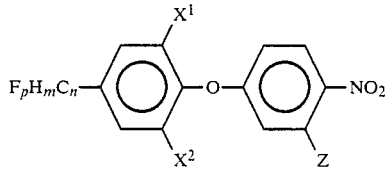

wherein
$X^1$, $X^2$ are independently selected hydrogen, halogen, trihalomethyl, cyano, or ($C_1$–$C_4$) alkyl, and
Z is selected from the group consisting of hydrogen, halogen, cyano, carboxy or salt thereof, alkylthio, carbalkoxy, carboxyalkyl, carbalkoxyalkyl, carbalkoxyalkoxycarbonyl, carbalkoxyalkoxy, alkoxy, cycloalkoxy, alkenyl, alkyl, cycloalkyl, unsubstituted or substituted amino, $R^2O$ in which $R^2$ represents a hydrogen atom or the ester bonded acid radical of an inorganic or organic oxyacid;
p is an integer from 1 to $2n+1$;
m is an integer of 0 to $2n$;
n is an integer of 1 to 5;
$m+p=2n+1$
and (B) a 3-isothiazolone.

Although Z can be as defined in U.S. Pat. Nos. 4,772,744 and 3,798,276, preferred are compositions wherein said compound (A) has no substituents selected from the group consisting of unsubstituted or substituted amino, $R^2O$ in which $R^2$ represents a hydrogen atom or the ester bonded acid radical of an inorganic or organic oxyacid, as are required by the aforementioned Ciba-Geigy reference.

More preferred are compositions wherein said compound (A) is of the formula

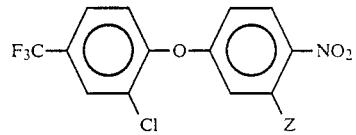

wherein Z is selected from the group consisting of alkoxy, carboxy or salt thereof, carbalkoxyalkoxy, and —$CO_2CH_2CO_2C_2H_5$.

The most preferred embodiment of compound (A) is oxyfluorfen which has the formula

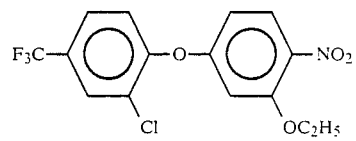

The preferred 3-isothiazolones are of the formula

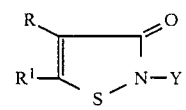

wherein
Y is an unsubstituted or substituted alkyl of from 1 to 18 carbon atoms, an unsubstituted or halo substituted alkenyl or alkynyl of from 2 to 8 carbon atoms, an unsubstituted or substituted cycloalkyl of from 5 to 8 carbon atoms, an unsubstituted or substituted aryl or hydrogen;
R is hydrogen, halo, or a ($C_1$–$C_4$)alkyl; and
$R^1$ is hydrogen, halo or a ($C_1$–$C_4$)alkyl.

Preferably, said Y is selected from the group consisting of methyl, ethyl, propyl, isopropyl, butyl, hexyl, octyl, cyclohexyl, benzyl, 3,4-dichlorobenzyl, 4-methoxybenzyl, 4-chlorobenzyl, hydroxymethyl, 3,4-dichlorophenyl, 4-methoxyphenyl, 4-chlorophenyl, chloromethyl, phenethyl, 2-(4-chlorophenyl)ethyl, chloropropyl, and hydrogen.

The most preferred isothiazolones are selected from the group consisting of 4,5-dichloro-2-octyl-3-isothiazolone, 2-octyl-3-isothiazolone, 5-chloro-2-methyl-3-isothiazolone, and 2-methyl-3-isothiazolone. Other isothiazolones which are preferred are as above wherein Y is ($C_1$–$C_{18}$) alkyl, ($C_3$–$C_{12}$) cycloalkyl, ($C_7$–$C_{10}$) aralkyl, or ($C_7$–$C_{10}$) ring-chlorinated aralkyl; R is hydrogen, methyl or chloro; and $R^1$ is hydrogen or chloro.

In accordance with the invention a method of controlling algae comprises using an effective amount of the aforementioned composition.

An especially useful aspect of the invention is in controlling algae in cooling tower water, and in a preferred embodiment, it is maintaining a concentration of about 0.005 to about 20 ppm of the anti-algal composition in the cooling tower water, preferrably a concentration of about 0.1 to 10 ppm, and most preferably a concentration of about 0.2 to 2 ppm.

Another important utility is in imparting algal resistance to a coating or impregnant composition comprising incorporation of the composition of the invention in the coating or impregnant, preferably at a concentration of about 0.1 ppm to about 2 percent, more preferably at concentration of about 1 ppm to 1 percent, and most preferably at a concentration of about 10 to 4000 ppm.

Algae-resistant coating or impregnant compositions provided by the invention preferably comprise about 0.1 ppm to about 2 percent of the antialgal composition, more preferably about 10 to 4000 ppm.

In a marine antifoulant composition, on the other hand, the antialgal composition of the invention comprises about 1 to 10 percent of the antifoulant composition.

The algal resistant compositions can also be used in construction products such as stucco, roof mastics, wall mastics, and masonry coatings for algae protection; in clear finishes and coatings to protect underlying substrates from algae; for algae control in aquaculture, including aquaria, fish hatcheries, shrimp ponds, finfish ponds, mollusc and crustacean cultivation; for algae control in recreational and decorative bodies of water such as swimming pools, lakes, fountains and decorative ponds; for algae control in bodies of water for industrial or municipal use, such as settling or separation ponds, waste treatment ponds, and water reservoirs; for algae control in hydroponic farming; for algae control in processing and manufacture of pulp and paper products; for inclusion in plastics or in coatings for plastics to protect against algae; and in plastics or coatings for plastics for swimming pool liners.

We prefer antialgal compositions wherein the weight ratio of (A) to (B) is about 0.1 to 100 to about 100 to 0.1.

Recent advances in molecular biology and taxonomy have provided for the distinction of photosynthetic procaryotic bacteria versus eucaryotic algae. In the past literature, the term "blue-green algae" made reference to a group of microorganisms which possessed chlorophyll and appeared blue-green in color. More recent textbooks on microbiology (Biology of Microorganisms, TD Brock, DW Smith, and MT Madigan, Prentice Hall, Inc. 1984) have distinguished these organisms from eucaryotic algae, such as the green algae, and considered them to be most appropriately classified as "blue-green bacteria" or "cyanobacteria". This distinction is made since the cell architecture more closely resembles the procaryotic bacteria than eucaryotic algae. Therefore, we refer herein to photosynthetic blue-green microorganisms as cyanobacteria or blue-green bacteria.

The following examples represent just a few of the many uses and compounds of the invention. They are intended to be illustrative but not limiting. Various modifications, alternatives, and improvements should become apparent to those skilled in the art without departing from the spirit and scope of the invention.

EXAMPLES

A. General Procedure

MIC values represent the Minimum Inhibitory Concentration. This is defined as the lowest level of compound required to completely inhibit (repress) the growth of a given organism.

A synergistic effect is defined as the response of two variables which is greater than the sum of both parts alone. Synergy was determined from combination studies with two compounds by the method of calculation described by F. C. Kull, P. C. Eisman, H. D. Sylwestrowicz and R. K. Mayer, *Applied Microbiology* 9,538 (1961):

$$\frac{Q_A}{Q_a} + \frac{Q_B}{Q_b} = \text{synergism index (SI)}$$

where:
$Q_a$=quantity of compound A, acting alone, producing an end point (MIC)
$Q_A$=quantity of compound A, in mixture, producing an end point (MIC)
$Q_b$=quantity of compound B, acting alone, producing an end point (MIC)
$Q_B$=quantity of compound B, in mixture, producing an end point (MIC)

The following SI values may be attained:
SI>1 represents antagonistic effect,
SI=1 represents additive effect,
SI<1 represents synergy.

Efficacy studies were conducted on a variety of microorganisms with oxyfluorfen and isothiazolone mixtures. The MIC studies were conducted using microtiter plate assays. In this method, a wide range of concentrations was tested by preparing two-fold serial dilutions of the compound in 96-well plastic microtiter plates. All liquid media transfers were performed with calibrated single or multichannel digital pipetters. Stock solutions of compounds were prepared in appropriate solvents and dispensed to the growth medium. All subsequent dilutions in plates were made using the desired growth medium; total volume of liquid in each well was 100 ul. Each plate contained a concentration of both compounds made by serially titrating equal volumes of liquids in two directions in the microtiter plate. Each plate contained a control row for each combination (one component only), hence, the individual compound MIC values were also determined.

The pure cultures used in this study were obtained from the Culture Collection of Algae at the University of Texas at Austin (UTEX). Microorganisms used as inocula were cultured in shaken liquid culture (Bristol's medium, pH 7.0, 25C, *Journal of Phycology*, 23s, 1–47, 1987 or Modified Allen's Media Formulation, described below) for one week or as needed to attain a desired cell mass. The cultures were then inoculated into the microtiter plates using a 96-prong multiple inoculator (5 μl inoculum); each well received a standard suspension of biomass (5% inoculum). Plates were incubated at 25° C. under constant illumination (500 ft candles). The extent of growth was determined under low magnification with the aid of microtiter plate reader. Growth in each cell was monitored periodically and growth/no-growth was recorded after 14 or 21 days. Results of each study were evaluated by calculating synergy index values (SI, previously described).

B. Preparation of Modified Allen's Media Formulation (pH 6.3)

| Component | Concentration (mg/l) |
| --- | --- |
| $NaNO_3$ | 250 |
| $CaCl_2(2H_2O)$ | 31 |
| $MgSO_4(7H_2O)$ | 75 |
| NaCl | 25 |
| $KH_2PO_4$ | 175 |
| $K_2HPO_4$ | 75 |
| $FeCl_3(6H_2O)$ | 7.5 |
| $Na_2(EDTA)$ | 10.3 |
| $Na_2B_4O_7(10H_2O)$ | 2.25 |
| $MnCl_2(4H_2O)$ | 0.90 |
| $ZnCl_2(7H_2O)$ | 0.11 |
| $CuCl_2(2H_2O)$ | 0.025 |
| $Na_2MoO_4(2H_2O)$ | 0.015 |
| $VOSO_4(2H_2O)$ | 0.015 |
| $CoCl_2(6H_2O)$ | 0.005 |

C. Isothiazolone Structure

Isothiazolones included in the examples are designated as follows:

(1) Isothiazolone A: 75% 5-chloro-2-methyl-3-isothiazolone plus 25% 2-methyl-3-isothiazolone
(2) Isothiazolone B: 4,5-dichloro-2-n-octyl-3-isothiazolone
(3) Isothiazolone C: 2-n-octyl-3-isothiazolone

EXAMPLE 1

Using a pure culture of *Chlorella pyrenoidosa* (green algae), various combinations of oxyfluorfen (acetone solution) and Isothiazolone A were subjected to MIC determinations (Bristol's Medium).

| Compound | MIC alone (ppm) | MIC combination (ppm) |
| --- | --- | --- |
| Oxyfluorfen | 0.125 | 0.016 |
| | | SI = 0.63 |
| Isothiazolone A | 0.50 | 0.25 |

EXAMPLE 2

In a manner similar to EXAMPLE 1, another MIC study was conducted with oxyfluorfen (acetone solution) and Isothiazolone A. Concentrations for oxyfluorfen ranged from 0.0019 to 2.0 ppm and for Isothiazolone A, from 0.0078 to 0.5 ppm (Modified Allen's Medium).

| Compound | MIC alone (ppm) | MIC combination (ppm) |
| --- | --- | --- |
| Oxyfluorfen | 1.0 | 0.125 |
| | | SI = 0.62 |
| Isothiazolone A | 0.25 | 0.125 |

EXAMPLE 3

In a manner similar to EXAMPLE 1, a pure culture of *Anabaena flos-aquae* (cyanobacteria) was used with various combinations of oxyfluorfen (acetone solution) and Isothiazolone B (Bristol's Medium).

| Compound | MIC alone (ppm) | MIC combination (ppm) |
| --- | --- | --- |
| Oxyfluorfen | >0.50* | 0.064 |
| | | SI = <0.61 |
| Isothiazolone B | 1.25 | 0.60 |

*exceeded the range tested in this experiment

EXAMPLE 4

In a manner similar to EXAMPLE 1, a pure culture of *Chlorella pyrenoidosa* was used with various combinations of oxyfluorfen (emulsifiable concentrate) and Isothiazolone B. Concentrations of oxyfluorfen ranged from 0.0019 to 2.0 ppm and for Isothiazolone B, from 0.0078 to 0.5 ppm (Modified Allen's Medium).

| Compound | MIC alone (ppm) | MIC combination (ppm) |
| --- | --- | --- |
| Oxyfluorfen | 2.0 | 1.0 |
| | | SI = 0.63 |
| Isothiazolone B | 0.06 | 0.008 |
| Oxyfluorfen | 2.0 | 0.25 |
| | | SI = 0.62 |
| Isothiazolone B | 0.06 | 0.03 |

EXAMPLE 5

In a manner similar to EXAMPLE 1, a pure culture of *Chlorella pyrenoidosa* was used with various combinations of oxyfluorfen (acetone solution) and Isothiazolone C. Concentrations for oxyfluorfen ranged from 0.0078 to 0.5 ppm and for Isothiazolone C, from 0.00049 to 0.5 ppm (Modified Allen's Medium).

| Compound | MIC alone (ppm) | MIC combination (ppm) |
| --- | --- | --- |
| Oxyfluorfen | 0.5 | 0.25 |
| | | SI = 0.62 |
| Isothiazolone C | 0.5 | 0.06 |
| Oxyfluorfen | 0.5 | 0.125 |
| | | SI = 0.75 |
| Isothiazolone C | 0.5 | 0.25 |

EXAMPLE 6

In a manner similar to EXAMPLE 5, a pure culture of *Chlorella pyrenoidosa* was used with various combinations of oxyfluorfen (emulsifiable concentrate) and Isothiazolone C. Concentrations for oxyfluorfen ranged from 0.00098 to 1.0 ppm and for Isothiazolone C, from 0.16 to 10.0 ppm (Modified Allen's Medium).

| Compound | MIC alone (ppm) | MIC combination (ppm) |
| --- | --- | --- |
| Oxyfluorfen | >1.0* | 0.25 |
| | | SI = 0.75 |
| Isothiazolone C | 1.25 | 0.63 |

*Exceeded the range tested in this experiment

We claim:

1. Composition useful for controlling algae comprising an effective amount of (A) a compound of the formula

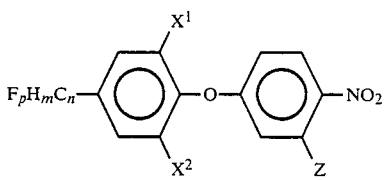

wherein
$X^1$, $X^2$ are independently selected from hydrogen, halogen, trihalomethyl, cyano, and ($C_1$ to $C_4$) alkyl;

Z is selected from the group consisting of hydrogen, halogen, cyano, carboxy or salt thereof, lower alkylthio, lower carbalkoxy, lower carboxyalkyl, lower carbalkoxyalkyl, lower carbalkoxyalkoxycarbonyl, lower carbalkoxyalkoxy, lower alkoxy, lower cycloalkoxy, lower alkenyl, lower alkyl, lower cycloalkyl, unsubstituted or substituted amino, $R^2O$ in which $R^2$ represents a hydrogen atom or the ester bonded acid radical of an inorganic or organic oxyacid;

p is an integer from 1 to $2n+1$;
m is an integer of 0 to $2n$;
n is an integer of 1 to 5;
$m+p=2n+1$ and (B) a 3-isothiazolone.

2. Composition of claim 1 wherein said compound (A) has no Z substituents selected from the group consisting of unsubstituted or substituted amino, $R^2O$ in which $R^2$ represents a hydrogen atom or the ester bonded acid radical of an inorganic or organic oxyacid.

3. Composition according to claim 1 wherein said compound (A) is of the formula

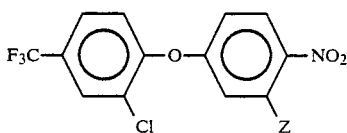

wherein Z is selected from the group consisting of alkoxy, carboxy or salt thereof, carbalkoxyalkoxy, and $-CO_2CH_2CO_2C_2H_5$.

4. Composition according to claim 1 wherein said compound (A) is oxyfluorfen of the formula

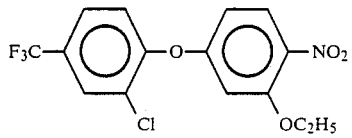

5. Composition according to claim 1 wherein said 3-isothiazolone is of the formula

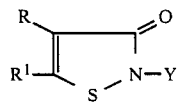

wherein
Y is an unsubstituted or substituted alkyl of from 1 to 18 carbon atoms, an unsubstituted or halo substituted alkenyl or alkynyl of from 2 to 8 carbon atoms, an unsubstituted or substituted cycloalkyl of from 5 to 8 carbon atoms, an unsubstituted or substituted aryl or hydrogen;
R is hydrogen, halo, or a ($C_1$-$C_4$)alkyl; and
$R^1$ is hydrogen, halo or ($C_1$-$C_4$)alkyl.

6. Composition according to claim 5 wherein said Y is selected from the group consisting of methyl, ethyl, propyl, isopropyl, butyl, hexyl, octyl, cyclohexyl, benzyl, 3,4-dichlorobenzyl, 4-methoxybenzyl, 3,4-dichlorophenyl, 4-methoxyphenyl, 4-chlorophenyl, 4-chlorobenzyl, hydroxymethyl, chloromethyl, phenethyl, 2-(4-chlorophenyl)ethyl, chloropropyl, and hydrogen.

7. Composition according to claim 6 wherein the isothiazolone is selected from the group consisting of 4,5-dichloro-2-octyl-3-isothiazolone, 2-octyl-3-isothiazolone, 5-chloro-2-methyl-3-isothiazolone, and 2-methyl-3-isothiazolone.

8. Composition according to claim 6 wherein Y is ($C_1$-$C_{18}$) alkyl, ($C_3$-$C_{12}$) cycloalkyl, ($C_7$-$C_{10}$) aralkyl, or ($C_7$-$C_{10}$) ring-chlorinated aralkyl; R is hydrogen, methyl or chloro; and $R^1$ is hydrogen or chloro.

9. Method of controlling algae comprising using an effective amount of the composition of claim 1.

10. Method of controlling algae in cooling tower water comprising maintaining a concentration of about 0.005 to about 20 ppm of the composition of claim 1 in the water.

11. Method of controlling algae in cooling tower water comprising maintaining a concentration of about 0.005 to about 20 ppm of the composition of claim 2 in the water.

12. Method of controlling algae in cooling tower water comprising maintaining a concentration of about 0.005 to about 20 ppm of the composition of claim 3 in the water.

13. Method of claim 12 wherein said concentration is about 0.1 to 10 ppm.

14. Method of claim 12 wherein said concentration is about 0.2 to 2 ppm.

15. Method of imparting algal resistance to a coating or impregnant composition comprising incorporation about 0.1 to about 2 percent of the composition of claim 1 in the coating or impregnant.

16. Method of claim 15 wherein said concentration is about 1 ppm to 1 percent.

17. Method of claim 16 wherein said concentration is about 10 ppm to 4000 ppm.

18. Marine antifoulant composition comprising about 1 to 10 percent of the composition of claim 1.

19. Composition of claim 1 wherein the weight ratio of (A) to (B) is about 0.1 to 100 to about 100 to 0.1.

20. Method of controlling algae in aquaculture, aquaria, fish hatcheries, shrimp ponds, finfish ponds, mollusc cultivation, and crustacean cultivation comprising using an effective amount of the composition of claim 1.

21. Method of controlling algae in swimming pools, lakes, spray ponds, fountains, or decorative ponds comprising using an effective amount of the composition of claim 1.

22. Method of controlling algae in settling ponds, separation ponds, waste treatment ponds, spray ponds, and water treatment ponds comprising using an effective amount of the composition of claim 1.

23. Method of controlling algae in hydroponic farming comprising using an effective amount of the composition of claim 1.

24. Method of controlling algae in a pulp or paper manufacturing process comprising using an effective amount of the composition of claim 1.

* * * * *